United States Patent [19]

Barnes et al.

[11] Patent Number: 4,464,373
[45] Date of Patent: Aug. 7, 1984

[54] 4,5-DIHYDROIMIDAZO-[1,2-A]QUINOXA-LINE-2-CARBOXYLIC ACIDS AND THEIR DERIVATIVES WITH ANTIALLERGIC ACTIVITY

[75] Inventors: Alan C. Barnes, Cirencester; David P. Kay, Purton; Peter D. Kennewell; Frederick L. Parker, both of Swindon; David A. Rowlands, Malmesbury, all of England

[73] Assignee: Roussel Uclaf, Paris, France

[21] Appl. No.: 487,617

[22] Filed: Apr. 22, 1983

[30] Foreign Application Priority Data

Apr. 28, 1982 [GB] United Kingdom ............... 8212325

[51] Int. Cl.³ ............... A61K 31/495; C07D 487/04
[52] U.S. Cl. ............... 424/250; 424/246; 424/248.4; 544/60; 544/120; 544/346; 544/225; 260/243.3
[58] Field of Search ............... 544/346; 424/250

[56] References Cited

U.S. PATENT DOCUMENTS 4,254,123  3/1981  Ramm et al. ............... 424/250
4,333,934  6/1982  Barnes et al. ............... 424/250

Primary Examiner—Donald G. Daus
Assistant Examiner—Cecilia Shen
Attorney, Agent, or Firm—Charles A. Muserlian

[57] ABSTRACT

Novel imidazoquinoxalines of the formula

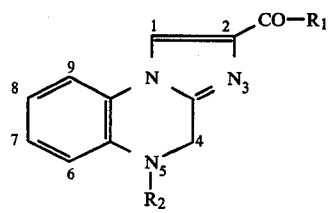

wherein $R_1$ is selected from the group consisting of hydroxy, alkoxy of 1 to 5 carbon atoms and cyclohexylcarbonyloxymethoxy, $R_2$ is selected from the group consisting of hydrogen, alkyl of 1 to 8 carbon atoms, alkoxycarbonylvinyl of 4 to 7 carbon atoms, —COR, —CONH(CH$_2$)$_n$—X and —A—(CH$_2$)$_m$—Y, R is selected from the group consisting of hydrogen, alkyl of 1 to 8 carbon atoms, cycloalkyl of 3 to 10 carbon atoms, alkenyl of 2 to 4 carbon atoms, alkoxy of 1 to 5 carbon atoms, alkoxycarbonyl of 2 to 5 carbon atoms, amino, —CF$_3$, —CHCl$_2$—, phenyl, aralkyl of 7 to 10 carbon atoms, aralkoxy of 7 to 10 carbon atoms, n is 0 and X is phenyl or n is an integer from 1 to 5 and X is selected from the group consisting of

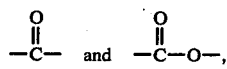

—S—C—NH$_3$⊕Hal⊖, 1,2,3-thiodiazolidinium chloride, and

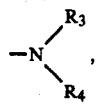

$R_3$ and $R_4$ are individually selected from the group consisting of hydrogen, alkyl of 1 to 5 carbon atoms, cycloalkyl of 3 to 7 carbon atoms, aryl of 6 carbon atoms and aralkyl of 7 to 8 carbon atoms or $R_3$ and $R_4$ taken together with the nitrogen atom to which they are attached form a saturated heterocycle with 4 to 8 ring carbon atoms optionally containing at least one oxygen atom or sulfur atom or nitrogen atom optionally substituted with alkyl of 1 to 3 carbon atoms or alkoxycarbonyl of 2 to 5 carbon atoms, Hal is chlorine or bromine, A is selected from the group consisting of $$-\overset{O}{\underset{\|}{C}}- \text{ and } -\overset{O}{\underset{\|}{C}}-O-,$$

m is a integer from 1 to 3, Y is

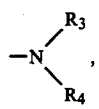

their non-toxic, pharmaceutically acceptable acid addition salts when $R_1$ is other than —OH and their salts with pharmaceutically acceptable metals or nitrogen bases when $R_1$ is —OH, having antiallergic properties.

20 Claims, No Drawings

4,5-DIHYDROIMIDAZO-[1,2-A]QUINOXALINE-2-CARBOXYLIC ACIDS AND THEIR DERIVATIVES WITH ANTIALLERGIC ACTIVITY

STATE OF THE ART

Commonly assigned U.S. Pat. No. 4,254,123 and U.S. Pat. No. 4,333,934 describe imidazolines of a different structure and describe therein other related prior art.

OBJECTS OF THE INVENTION

It is an object of the invention to provide the novel compounds of formula I and their non-toxic, pharmaceutically acceptable acid addition salts and salts.

It is another object of the invention to provide novel antiallergric compositions and to provide a novel method of combatting allergic symptoms in warm-blooded animals.

These and other objects and advantages of the invention will become obvious from the following detailed description.

THE INVENTION

The novel compounds of the invention are selected from the group consisting of imidazoquinoxalines of the formula

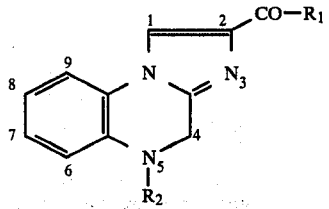

wherein $R_1$ is selected from the group consisting of hydroxy, alkoxy of 1 to 5 carbon atoms and cyclohexylcarbonyloxymethoxy, $R_2$ is selected from the group consisting of hydrogen, alkyl of 1 to 8 carbon atoms, alkoxycarbonylvinyl of 4 to 7 carbon atoms, —COR, —CONH(CH$_2$)$_n$—X and —A—(CH$_2$)$_m$—Y, R is selected from the group consisting of hydrogen alkyl of 1 to 8 carbon atoms, cycloalkyl of 3 to 10 carbon atoms, alkenyl of 2 to 4 carbon atoms, alkoxy of 1 to 5 carbon atoms, alkoxycarbonyl of 2 to 5 carbon atoms, amino, —CF$_3$, —CHCl$_2$—, phenyl, aralkyl of 7 to 10 carbon atoms, aralkoxy of 7 to 10 carbon atoms and when $R_2$ is —CONH—(CH$_2$)$_n$—X, n is 0 and X is phenyl or n is an integer from 1 to 5 and X is selected from the group consisting of

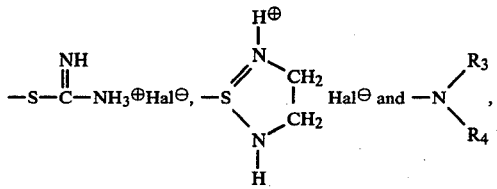

$R_3$ and $R_4$ are individually selected from the group consisting of hydrogen, alkyl of 1 to 5 carbon atoms, cycloalkyl of 3 to 7 carbon atoms, aryl of 6 carbon atoms and aralkyl of 7 to 8 carbon atoms or $R_3$ and $R_4$ taken together with the nitrogen atom to which they are attached form a saturated heterocycle with 4 to 8 ring carbon atoms optionally containing at least one oxygen atom or sulfur atom or nitrogen atom optionally substituted with alkyl of 1 to 3 carbon atoms or alkoxycarbonyl of 2 to 5 carbon atoms, Hal is chlorine or bromine, A is selected from the group consisting of

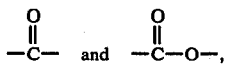

m is a integer from 1 to 3, Y is

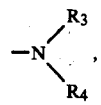

their non-toxic, pharmaceutically acceptable acid addition salts when $R_1$ is other than —OH and their salts with pharmaceutically acceptable metals or nitrogen bases when $R_1$ is —OH.

Examples of alkoxy of 1 to 5 carbon atoms are methoxy, ethoxy, propoxy, isopropoxy and butoxy and examples of alkyl of 1 to 8 carbon atoms are methyl, ethyl, n-propyl, isopropyl, n-butyl, isobutyl, tert.-butyl, n-pentyl, isopentyl, n-hexyl, n-heptyl and 1-ethylpentyl. Examples of alkoxycarbonylvinyl of 4 to 7 carbon atoms include methoxycarbonylvinyl and ethoxycarbonylvinyl and examples of cycloalkyl of 3 to 10 carbon atoms include cyclopropyl, cyclobutyl, cyclopentyl, cyclohexyl, cycloheptyl and adamantyl. Examples of alkenyl of 2 to 4 carbon atoms are vinyl and allyl. Examples of alkoxycarbonyl of 2 to 5 carbon atoms include methoxycarbonyl and ethoxycarbonyl.

Examples of aralkyl and aralkoxy of 7 to 10 carbon atoms are benzyl, phenethyl, benzyloxy and phenethoxy. Aryl and aralkyl of 6 to 8 carbon atoms include phenyl, benzyl and phenethyl. Examples of the saturated heterocycles of 4 to 8 carbon ring atoms as defined above include pyrrolidino, piperidino, 2,3,4,5,6,7-hexahydroazepino, tropanyl, morpholino, thiomorpholino and piperazin-1-yl.

Examples of suitable acids to form acid addition salts of the compounds of formula I when $R_1$ is other than hydroxy are inorganic acids such as hydrochloric acid, hydrobromic acid, hydroiodic acid, nitric acid, sulfuric acid or phosphoric acid, or organic acids such as acetic acid, formic acid, benzoic acid, maleic acid, fumaric acid, succinic acid, tartaric acid, citric acid, oxalic acid, glyoxylic acid and aspartic acid, alkanesulfonic acids such as methanesulfonic acid and arylsulfonic acids such as benzenesulfonic acid.

The compounds of formula I wherein $R_1$ is hydroxy have an acidic character and can form salts with metals or nitrogen bases. Examples of suitable salts are those with alkali metals such as sodium, potassium or lithium, alkaline earth metals such as calcium and metals such as magnesium or aluminum and with nitrogen bases such as ammonia and amines such as tromethamines, triethanolamine, lysine and arginine.

Among the preferred compounds of the invention are the compounds of formula I wherein $R_1$ is —OH or alkoxy of 1 to 5 carbon atoms, especially ethoxy, those wherein $R_2$ is hydrogen, alkyl of 1 to 8 carbon atoms, —COR, —CONH—(CH$_2$)$_n$—X, or —A—(CH$_2$)$_m$—Y and R is alkyl of 1 to 8 carbon atoms, cycloalkyl of 3 to 10 carbon atoms, vinyl, alkoxy of 1 to 5 carbon atoms, phenyl or benzyloxy, n is 2 and X is

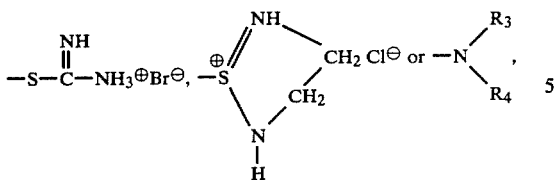

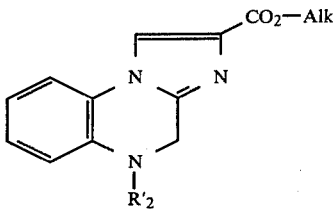

$R_3$ and $R_4$ are individually hydrogen, alkyl of 1 to 5 carbon atoms or $R_3$ and $R_4$ with the nitrogen atom form pyrrolidino, piperidino, morpholino, thiomorpholino, piperazinyl, methylpiperazinyl or ethoxycarbonylpiperazinyl, A is —CO— or —$CO_2$—, m is 1 or 2, Y has the above definition and the salts and acid addition salts thereof.

Especially preferred compounds of the invention are those of formula I wherein $R_1$ is —OH or ethoxy and $R_2$ is —COR and R is alkyl of 1 to 8 carbon atoms or alkoxy of 1 to 5 carbon atoms and their salts and acid addition salts. Specific preferred compounds are diethyl 4,5-dihydroimidazo[1,2-a]quinoxalin-2,5-dicarboxylate and 4,5-dihydro-5-ethoxycarbonylimidazo[1,2-a]quinoxalin-2-carboxylic acid and its tromethamine salts.

Compounds of formula I as defined above wherein $R_1$ is alkoxy of 1 to 5 carbon atoms and $R_2$ is hydrogen, i.e. compounds of the formula

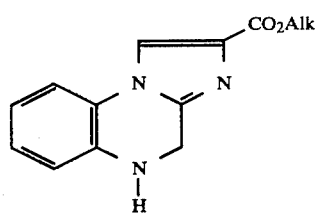

wherein Alk is alkyl of 1 to 5 carbon atoms may be prepared by reduction of a compound of the formula

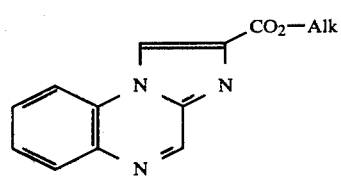

wherein Alk is as defined above. The reduction may be performed with conventional reducing agents e.g. sodium borohydride, sodium cyanoborohydride or 10% palladium-charcoal and hydrogen in the presence of an organic solvent such as for example an alcohol like ethanol or tetrahydrofuran. The compound of formula $I_A$ may be isolated and converted, if desired, to an acid addition salt in the conventional manner.

Compounds of formula $I_A$ may be used as intermediates in the preparation of other compounds of the invention. For example, compounds of formula I and the acid addition salts threof wherein $R_1$ is alkoxy of 1 to 5 carbon atoms and $R_2$ has the above definition but excluding compounds wherein $R_2$ is hydrogen or —CHO, —CO—NH—$(CH_2)_n$—X or —A—$(CH_2)_m$—Y as defined above i.e. compounds of the formula wherein Alk has the above defined meaning and $R_2'$ is as defined above for $R_2$ with the exception of hydrogen and —CHO, —CO—NH—$(CH_2)_n$—X and —A—$(CH_2)_m$—Y as defined above may be prepared by reaction of a compound of formula $I_A$ as defined above with a compound of the formula $$Z\text{—}R_2' \qquad \text{III}$$

wherein $R_2'$ is a defined above and Z is a halogen atom, e.g. chlorine or bromine, followed, if desired, by formation of an acid addition salt in the conventional manner. The reaction between the compounds of formulae $I_A$ and III is preferably performed under anhydrous conditions in the presence of an organic solvent, e.g. dimethylformamide, toluene or tetrahydrofuran, chlorinated solvents, e.g. dichloromethane, chloroform or dichloroethane, if desired with the addition of an inorganic base, e.g. sodium or potassium carbonate. The compounds of formula $I_A$ may be converted into the compounds of formula $I_B$ in this manner if desired without intermediate isolation of the compound of formula $I_A$.

Compounds of formula I wherein $R_1$ is alkoxy of 1 to 5 carbon atoms and $R_2$ is a straight-or branched-chain alkyl of 1 to 8 carbon atoms may also be prepared by reductive alkylation of a compound of formula $I_A$ using a corresponding aldehyde or ketone to introduce the $R_2$ in the 5-position. This reaction is generally performed by hydrogenation under acid conditions in the presence of a hydrogenation catalyst, for example palladium/carbon.

Compounds of formula I wherein $R_1$ is alkoxy of 1 to 5 carbon atoms and $R_2$ is —CO—R may be prepared by reaction of a compound of formula $I_A$ with an acid of the formula OH—CO—R wherein R is as defined above, preferably in the presence of an organic solvent e.g. dichloromethane and advantageously in the presence of an activating agent e.g. carbonyldiimidazole. Thus, for example compounds of formula I wherein $R_2$ is —CHO may be prepared using formic acid.

Compounds of formula I above wherein $R_1$ is alkoxy of 1 to 5 carbon atoms and $R_2$ is —CO—NH—$(CH_2)_n$—X and acid addition salts thereof may be prepared when n=0 and X is phenyl by reacting a compound of formula $I_A$ as defined above with phenyl isocyanate followed, if desired, by formation of an acid addition salt in the conventional manner. The reaction of the compound of formula $I_A$ with phenyl isocyanate is preferably carried out in the presence of an organic solvent, e.g. toluene, tetrahydrofuran, dichloromethane or dichloroethane under anhydrous conditions at reflux temperature.

Compounds of the invention wherein $R_1$ is alkoxy of 1 to 5 carbon atoms and $R_2$ is —CO—NH—$(CH_2)_{n'}$—X' wherein n' is an integer from 1 to 5 and X' is as defined above for X other than phenyl may be prepared for example by reaction of a compound of the formula ![Structure V: benzene fused to dihydropyrazine with CO2-Alk and CO-NH-(CH2)n'-Q substituents]

$$\text{Structure V}$$

wherein n' and Alk are as defined above and Q is halogen e.g. chlorine or bromine with a compound of the formula

H—X'      VI wherein X' has the above defined meaning to obtain a compound of the formula ![Structure Ic]

$$\text{Structure } I_C$$

wherein n', Alk and X' have the above-defined meanings followed, if desired, by formation of an acid addition salt in the conventional manner. The reaction between the compounds of formulae V and VI is preferably effected in the presence of an organic solvent, e.g. toluene, tetrahydrofuran, dichloromethane or dichloroethane under anhydrous conditions at reflux temperature.

Compounds of formula V above may be prepared by reaction of a compound of formula $I_A$ as defined above with an isocyanate of the formula Q—(CH$_2$)$_{n'}$—N=C=O      IV wherein n' and Q are as defined above. This reaction is preferably carried out in the presence of an organic solvent, e.g. toluene, tetrahydrofuran, dichloromethane or dichloroethane under anhydrous conditions at reflux temperature.

Compounds of formula V above are novel and constitute further features of the invention. Such compounds may themselves possess a certain amount of medically interesting activity.

Compounds of formula I wherein $R_1$ is alkoxy of 1 to 5 carbon atoms and $R_2$ is —A—(CH$_2$)$_m$—Y wherein A, m and Y are as defined above and acid addition salts thereof may be prepared by reacting a compound of the formula ![Structure IX]

$$\text{Structure IX}$$

wherein Alk, A, m and Q are as defined above with a compound of the formula

H—Y      X wherein Y has the above defined meaning to obtain a compound of the formula ![Structure Id]

$$\text{Structure } I_D$$

wherein A, Alk, m and Y have the above defined meanings followed, if desired, by formation of acid addition salts in the conventional manner. The above reaction is preferably carried out under anhydrous conditions in the presence of an organic solvent, e.g. toluene, tetrahydrofuran, dichloromethane or dichloroethane.

Compounds of formula IX as defined above may be prepared by reaction of a compound of formula $I_A$ as defined above with a compound of the formula Q—A—(CH$_2$)$_m$—Q      VII wherein Q, A and m are as hereinafter defined. This reaction is preferably carried out under anhydrous conditions in the presence of an organic solvent e.g. dimethylformamide, toluene or tetrahydrofuran, chlorinated solvents, e.g. dichloromethane, chloroform or dichloroethane, if desired with the addition of an inorganic base, e.g. sodium or potassium carbonate.

Compounds of formula IX above are novel and constitute further features of the invention and such compounds may themselves possess a certain amount of medically interesting activity.

Compounds of formula I as defined above wherein $R_1$ is hydroxy and salts thereof may be prepared by saponification of an ester of the formula ![Structure I']

$$\text{Structure } I'$$

wherein $R_2$ and Alk are as hereinbefore defined to yield a compound of the formula ![Structure I'']

$$\text{Structure } I''$$

wherein $R_2$ is as hereinbefore defined followed, if desired, by formation of a salt in the conventional manner.

The saponification is preferably carried out using a metal hydroxide, e.g. an alkali metal hydroxide such as sodium hydroxide, in the presence of an alcohol e.g. ethanol.

Compounds of formula I″ may be used as intermediates in the preparation of compounds of formula I wherein $R_1$ is cyclohexylcarbonyloxymethoxy and such compounds may be prepared by reaction of compound of formula I″ as defined above with cyclohexylcarbonyloxymethanol in the presence of an alkali metal carbonate, e.g. lithium carbonate, preferably in a solvent such as dimethylformamide.

Acid addition salts of the compounds of formula I wherein $R^1$ is other than hydroxy may be prepared by reacting the said compounds of formula I with an appropriate acid, preferably in substantially equimolar proportions. Salts with metals or nitrogen bases of compounds of formula I wherein $R_1$ is hydroxy may be prepared by reacting a compound of formula I in which $R_1$ is hydroxy with an appropriate base.

The antiallergic compositions of the invention are comprised of an antiallergically effective amount of at least one compound of formula I and their salts and non-toxic, pharmaceutically acceptable acid addition salts and an inert pharmaceutical carrier. The compositions may be in the form of solids or liquids such as tablets, dragees, gelatin capsules, granules, suppositories, syrups, aerosols, creams, ointments and injectable solutions or suspensions.

Examples of suitable excipients are talc, arabic gum, lactose, starch, magnesium stearate, cocoa butter, aqueous or non-aqueous vehicles, animals and vegetable fats, paraffin derivatives, glycols, various wetting, dispersing or emulsifying agents and preservatives.

Advantageously, the compositions may be formulated as dosage units, each unit being adapted to supply a fixed dose of active ingredient. Suitable dosage units for adult human treatment may contain from 0.1 to 1000 mg, preferably from 1 to 100 mg of active ingredient and the daily dosage will vary depending on the product employed but will generally be in the range of 0.25 to 100 mg per day for oral administration for adult human treatment.

The compositions because of their antiallergic activity are useful for the treatment of allergic asthma and asthmatiform bronchitis of allergic origin.

Among the preferred compositions of the invention are those wherein the active ingredient are compounds of formula I wherein $R_1$ is —OH or alkoxy of 1 to 5 carbon atoms, especially ethoxy, those wherein $R_2$ is hydrogen, alkyl of 1 to 8 carbon atoms, —COR, —CONH—$(CH_2)_n$—X or —A—$(CH_2)_m$—Y and R is alkyl of 1 to 8 carbon atoms, cycloalkyl of 3 to 10 carbon atoms, vinyl, alkoxy of 1 to 5 carbon atoms, phenyl or benzyloxy, n is 2 and X is

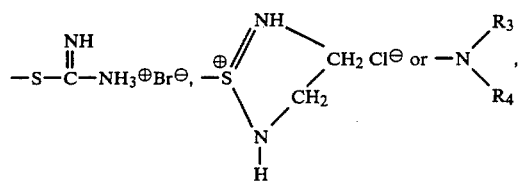

$R_3$ and $R_4$ are individually hydrogen, alkyl of 1 to 5 carbon atoms or $R_3$ and $R_4$ with the nitrogen atom form pyrrolidino, piperidino, morpholino, thiomorpholino, piperazinyl, methylpiperazinyl or ethoxycarbonylpiperazinyl, A is —CO— or —$CO_2$, m is 1 or 2, Y has the above definition and the salts and acid addition salts thereof.

Especially preferred are the compositions of the invention wherein the active ingredient is a compound of formula I wherein $R_1$ is —OH or ethoxy and $R_2$ is —COR and R is alkyl of 1 to 8 carbon atoms or alkoxy of 1 to 5 carbon atoms and their salts and acid addition salts, and among them those wherein the active ingredient is one of the specific preferred compounds mentioned above.

The novel method of the invention for preventing or relieving allergic symptoms in warm-blooded animals, including humans, comprises administering to warm-blooded animals an antiallergically effective amount of at least one compound of formula I and its salts and non-toxic, pharmaceutically acceptable acid addition salts. The said compounds may be administered orally, rectally, parenterally or topically and the usual daily dose is 0.003 to 15 mg/kg depending on the compound and the condition being treated.

The novel intermediates of the invention are those of formulae V and IX and the starting materials of formula II may be prepared by the process described in British patent application Ser. No. 79-26597, and U.S. Pat. No. 4,254,123.

In the following examples there are described several preferred embodiments to illustrate the invention and it is to be understood that the invention is not intended to be limited to the specific embodiments.

EXAMPLE 1

Ethyl 4,5-dihydroimidazo[1,2-a]quinoxaline-2-carboxylate

To a stirred solution of 1.6 g of ethyl imidazo[1,2-a]quinoxaline-2-carboxylate hydrobromide (British patent application Ser. No. 79-26597, in 50 ml of ethanol was added portionwise 0.5 g of sodium borohydride and at the completion of the reaction (tlc), the mixture was poured into 250 ml of water. The mixture was extracted with ethyl acetate and the organic layer was washed with water, dried and evaporated to dryness to obtain 1.2 g (97% yield) of ethyl 4,5-dihydroimidazo[1,2-a]quinoxaline-2-carboxylate melting at 206°–8° C.

EXAMPLE 2

Ethyl 4,5-dihydro-5-(diethylaminoacetyl)imidazo[1,2-a]quinoxaline-2-carboxylate

STEP A: Ethyl 4,5-dihydro-5-chloroacetylimidazo[1,2-a]quinoxaline-2-carboxylate

A solution of 2 g of ethyl 4,5-dihydroimidazo[1,2-a]quinoxaline-2-carboxylate in 20 ml of dry dimethylformamide was treated with 2 ml of chloroacetyl chloride and the mixture was stirred overnight. A white solid settled out and was filtered off and crystallized from ethanol to obtain 2.27 g (86% yield) of ethyl 4,5-dihydro-5-chloroacetylimidazo[1,2-a]quinoxaline-2-carboxylate melting at 178°–83° C.

STEP B: Ethyl 4,5-dihydro-5-(diethylaminoacetyl)imidazo[1,2-a]quinoxaline-2-carboxylate A solution of 0.8 g of ethyl 4,5-dihydro-5-chloroacetylimidazo[1,2-a]quinoxaline-2-carboxylate in 40 ml of dry toluene was treated with 10 ml of diethylamine and the mixture was stirred overnight at room temperature and then at 60° C. for b 4 hours. The mixture was poured into water and was extracted with ethyl acetate. The organic phase was washed with water, dried and evaporated to obtain a pale yellow oil. This was chromatographed over silica gel with chloroform as eluant to give in the first two fractions of 0.8 g (90% yield) of 4,5-dihydro-5-(diethylaminoacetyl)imidazo[1,2-a]quinoxaline-2-carboxylate melting at 116°-8° C.

EXAMPLE 3

Diethyl 4,5-dihydroimidazo[1,2-a]quinoxaline-2,5-dicarboxylate

A solution of 1.0 g of ethyl 4,5-dihydroimidazo[1,2-a]quinoxaline-5-carboxylate in 5 ml of dry dimethylformamide was treated with 0.5 g of ethyl chloroformate and the mixture was stirred at room temperature. After 2 hours, the mixture was set solid, was filtered and the residue was triturated with water and chromatographed over silica gel with ethyl acetate as eluant to obtain 0.98 g (76% yield) of diethyl 4,5-dihydroimidazo[1,2-a]quinoxaline-2,5-dicarboxylate melting at 151°-3° C.

EXAMPLE 4

Ethyl 4,5-dihydro-5-(phenylcarboxamido)imidazo[1,2-a]quinoxaline-2-carboxylate

A suspension of 1 g of ethyl 4,5-dihydroimidazo[1,2-a]quinoxaline-2-carboxylate in 10 ml of dry toluene was treated with phenyl isocyanate and the mixture was refluxed. After 1 hour, the suspension was cooled, filtered and the solid crystallized from ethanol to obtain 1.39 g (93% yield) of ethyl 4,5-dihydro-5-(phenylcarboxamido)imidazo[1,2-a]quinoxaline-2-carboxylate melting at 213°-5° C.

EXAMPLE 5

Ethyl 4,5-dihydro-5-(morpholinoethylcarboxamido)imidazo[1,2-a]quinoxaline-2-carboxylate STEP A: Ethyl 4,5-dihydro-5-(chloroethylcarboxamido)imidazo[1,2-a]quinoxaline-2-carboxylate The title compound was prepared from ethyl 4,5-dihydroimidazo[1,2-a]quinoxaline-2-carboxylate and chloroethylisocyanate following the method of Example 4.

STEP B: Ethyl 4,5-dihydro-5-(morpholinoethylcarboxamido)imidazo[1,2-a]quinoxaline-2-carboxylate To a solution of ethyl 4,5-dihydro-5-(chloroethylcarboxamido)-imidazo[1,2-a]quinoxaline-2-carboxylate (prepared as in Step A) in 100 ml of dry toluene was added 1 ml of morpholine and the mixture was refluxed for 6 hours. After cooling, the solution was filtered to remove morpholine hydrochloride and the filtrate was concentrated to dryness. The residue was chromatographed over silica gel with chloroform-methanol (97:3) as eluant to obtain 0.21 g (30.5% yield) of ethyl 4,5-dihydro-5-(morpholinoethylcarboxamido)imidazo[1,2-a]quinoxaline-2-carboxylate melting at 180°-3° C.

EXAMPLE 6

4,5-dihydro-5-(methoxycarbonyl)imidazo[1,2-a]quinoxaline-2-carboxylic acid

A solution of 1.1 g of ethyl 4,5-dihydro-5-(methoxycarbonyl)imidazo[1,2-a]quinoxaline-2-carboxylate in 18 ml of ethanol and 6 ml of water were stirred at 50° C. overnight with 4 ml of 1N NaOH. 1 ml of 1N sodium hydroxide was added and stirring was continued for a further 3 hours. Acidification with conc. HCl gave a white solid which was crystallized from methanol to obtain 0.6 g (60% yield) of 4,5-dihydro-5-(methoxycarbonyl)imidazo[1,2-a]quinoxaline-2-carboxylic acid melting at 204°-8° C.

EXAMPLES 7 to 44

Using a method similar to that used in Examples 1 to 6 but starting from the corresponding compound of formula $I_A$, the following compounds of Examples 7 to 20 and 23-43 were prepared. The methods used for Examples 21, 22 and 44 are given hereinafter.

Example 7: Ethyl 5-acetyl-4,5-dihydroimidazo[1,2-a]quinoxaline-2-carboxylate.

Example 8: Ethyl 4,5-dihydro-5-(benzyloxycarbonyl)imidazo[1,2-a]quinoxaline-2-carboxylate.

Example 9: Ethyl 4,5-dihydro-5-(methoxycarbonyl)imidazo[1,2-a]quinoxaline-2-carboxylate.

Example 10: Ethyl 4,5-dihydro-5-(piperidinoacetyl)imidazo[1,2-a]quinoxaline-2-carboxylate.

Example 11: Ethyl 4,5-dihydro-5-(propyloxycarbonyl)imidazo[1,2-a]quinoxaline-2-carboxylate.

Example 12: Ethyl 4,5-dihydro-5-(butyloxycarbonyl)imidazo[1,2-a]quinoxaline-2-carboxylate.

Example 13: Ethyl 4,5-dihydro-5-piperidinoethylcarboxamido)imidazo[1,2-a]quinoxaline-2-carboxylate hydrochloride.

Example 14: Ethyl 4,5-dihydro-5-(diethylaminoethylcarboxamido)imidazo[1,2-a]quinoxaline-2-carboxylate.

Example 15: 4,5-dihydro-5-(ethoxycarbonyl)imidazo[1,2-a]quinoxaline-2-carboxylic acid.

Example 16: Ethyl 5-isobutyryl-4,5-dihydroimidazo[1,2-a]quinoxaline-2-carboxylate.

Example 17: Ethyl 5-cyclopropanoyl-4,5-dihydroimidazo[1,2-a]quinoxaline-2-carboxylate.

Example 18: Ethyl 5-benzoyl-4,5-dihydroimidazo[1,2-a]quinoxaline-2-carboxylate.

Example 19: Ethyl 5-propionyl-4,5-dihydroimidazo[1,2-a]quinoxaline-2-carboxylate.

Example 20: Ethyl 5-cyclopentanoyl-4,5-dihydroimidazo[1,2-a]quinoxaline-2-carboxylate.

Example 21: Ethyl 5-methyl-4,5-dihydroimidazo[1,2-a]quinoxaline-2-carboxylate.

Example 22: Ethyl 5-ethyl-4,5-dihydroimidazo[1,2-a]quinoxaline-2-carboxylate hydrochloride.

Example 23: Ethyl 4,5-dihydro-5-(N-methylpiperazinoethyl)carboxamido)imidazo[1,2-a]quinoxaline-2-carboxylate.

Example 24: Ethyl 4,5-dihydro-5(N-ethoxycarbonylpiperazinoethylcarboxamido)imidazo[1,2-a]quinoxaline-2-carboxylate hydrochloride.

Example 25: (2-ethoxycarbonyl-4,5-dihydroimidazo[1,2-a]quinoxaline-5-yl)-2'-ethylcarboxamidothiouronium chloride.

Example 26: Ethyl 4,5-dihydro-5-trimethylacetylimidazo[1,2-a]quinoxaline-2-carboxylate.

Example 27: Ethyl 4,5-dihydro-5-(2-morpholinoethoxycarbonyl)imidazo[1,2-a]quinoxaline-2-carboxylate hydrochloride.

Example 28: Ethyl 5-acryloyl-4,5-dihydroimidazo[1,2-a]quinoxaline-2-carboxylate.

Example 29: Ethyl 5-cyclobutanoyl-4,5-dihydroimidazo[1,2-a]quinoxaline-2-carboxylate.

Example 30: Ethyl 5-di-n-butylaminoethylcarboxamido-4,5-dihydroimidazo[1,2-a]quinoxaline-2-carboxylate hydrochloride.

Example 31: Ethyl 5-butanoyl-4,5-dihydroimidazo[1,2-a]quinoxaline-2-carboxylate.

Example 32: Ethyl 5-trifluoroacetyl-4,5-dihydroimidazo[1,2-a]quinoxaline-2-carboxylate.

Example 33: Cyclohexylcarbonyloxymethyl 5-ethoxycarbonyl-4,5-dihydroimidazo[1,2-a]quinoxaline-2-carboxylate.

Example 34: Ethyl 5-dichloroacetyl-4,5-dihydroimidazo[1,2-a]quinoxaline-2-carboxylate.

Example 35: Ethyl 4,5-dihydro-5-(2-ethoxycarbonylvinyl)imidazo[1,2-a]quinoxaline-2-carboxylate.

Example 36: Ethyl 5-(bromopropionyl)-4,5-dihydroimidazo[1,2-a]quinoxaline-2-carboxylate.

Example 37: Ethyl 5-(1-adamantoyl)-4,5-dihydroimidazo[1,2-a]quinoxaline-2-carboxylate.

Example 38: Ethyl 5-(2-ethylhexanoyl)-4,5-dihydroimidazo[1,2-a]quinoxaline-2-carboxylate.

Example 39: Ethyl 4,5-dihydro-5-(2-methylpiperazino)ethoxycarbonyl)imidazo[1,2-a]quinoxaline-2-carboxylate dihydrochloride.

Example 40: Ethyl 4,5-dihydro-5-(2-piperidinoethoxycarbonyl)imidazo[1,2-a]quinoxaline-2-carboxylate hydrochloride.

Example 41: Ethyl 4,5-dihydro-5-(ethoxyalyl)-imidazo[1,2-a]quinoxaline-2-carboxylate.

Example 42: Ethyl 4,5-dihydro-5-carbamoylimidazo[1,2-a]quinoxaline-2-carboxylate.

Example 43: Tris(hydroxymethyl)methanammonium 4,5-dihydro-5-(ethoxycarbonyl)imidazo[1,2-a]quinoxaline-2-carboxylate.

Example 44: Ethyl 5-formyl-4,5-dihydroimidazo[1,2-a]quinoxaline-2-carboxylate.

Experimental data for all the compounds of Examples 1 to 44 is given in the following Table 1. Table 1 also indicates for Examples 7 to 44 the method used for the preparation of the compound, as illustrated in one of Examples 1 to 6 or in Examples 22 and 44 hereinafter.

TABLE 1

| Example | $R_1$ | $R_2$ | Prepared as in Example | M.pt (°C.) | Formula | Calc. %C | Calc. %H | Calc. %N | Found %C | Found %H | Found %N |
|---|---|---|---|---|---|---|---|---|---|---|---|
| 1 | $OC_2H_5$ | H | — | 206–8 | $C_{13}H_{13}N_3O_2$ | 64.19 | 5.39 | 17.27 | 64.01 | 5.48 | 17.25 |
| 2A | $OC_2H_5$ | $COCH_2Cl$ | — | 178–183 | $C_{15}H_{14}ClN_3O_3$ | 56.35 | 4.41 | 13.14 | 56.32 | 4.48 | 13.19 |
| 2B | $OC_2H_5$ | $COCH_2NEt_2$ | — | 116–8 | $C_{19}H_{24}N_4O_3$ | 64.03 | 6.79 | 15.72 | 63.82 | 6.81 | 15.69 |
| 3 | $OC_2H_5$ | $CO_2Et$ | — | 151–3 | $C_{16}H_{17}N_3O_4$ | 60.94 | 5.43 | 13.33 | 60.74 | 5.38 | 13.26 |
| 4 | $OC_2H_5$ | CONHPh | — | 213–5 | $C_{20}H_{18}N_4O_3$ | 66.29 | 5.01 | 15.46 | 66.19 | 5.09 | 15.42 |
| 5A | $OC_2H_5$ | $CONH(CH_2)_2Cl$ | 4 | 183–5 | $C_{16}H_{17}ClN_4O_3$ | 55.10 | 4.91 | 16.06 | 54.64 | 5.01 | 15.78 |
| 5B | $OC_2H_5$ | $CONH(CH_2)_2N$⟨morpholine⟩ | — | 180–3 | $C_{20}H_{25}N_5O_4$ | 60.14 | 6.31 | 17.53 | 59.84 | 6.24 | 17.43 |
| 6 | OH | $CO_2CH_3$ | — | 204–208 | $C_{13}H_{11}N_3O_4 \cdot 0.5 H_2O$ | 55.32 | 4.29 | 14.88 | 56.00 | 4.20 | 14.77 |
| 7 | $OC_2H_5$ | $COCH_3$ | 2A | 137–140 | $C_{15}H_{13}N_3O_3$ | 63.15 | 5.30 | 14.73 | 63.00 | 5.31 | 14.72 |
| 8 | $OC_2H_5$ | $CO_2CH_2Ph$ | 3 | 151–3 | $C_{21}H_{19}N_3O_4$ | 66.83 | 5.07 | 11.13 | 66.77 | 5.12 | 10.96 |
| 9 | $OC_2H_5$ | $CO_2CH_3$ | 3 | 193–4 | $C_{15}H_{15}N_3O_4$ | 59.80 | 5.02 | 13.95 | 59.64 | 5.07 | 13.98 |
| 10 | $OC_2H_5$ | $COCH_2N$⟨piperidine⟩ | 2B | dec. ca. 200 | $C_{20}H_{22}N_4O_3 \cdot HCl \cdot 2H_2O$ | 54.48 | 6.63 | 12.71 | 54.37 | 6.63 | 12.60 |
| 11 | $OC_2H_5$ | $CO_2(CH_2)_2CH_3$ | 3 | 135–7 | $C_{17}H_{21}N_3O_4$ | 62.00 | 5.81 | 12.76 | 61.87 | 5.76 | 12.72 |
| 12 | $OC_2H_5$ | $CO_2(CH_2)_3CH_3$ | 3 | 129–32 | $C_{18}H_{21}N_3O_4$ | 63.06 | 6.14 | 12.24 | 63.06 | 6.14 | 12.21 |
| 13 | $OC_2H_5$ | $CONH(CH_2)_2N$⟨piperidine⟩ | 5 | 180–5 | $C_{21}H_{29}N_5O_3Cl_2 \cdot 2H_2O$ | 51.64 | 6.40 | 14.34 | 51.46 | 6.10 | 14.08 |
| 14 | $OC_2H_5$ | $CONH(CH_2)_2NEt_2$ | 5B | 164–6 | $C_{20}H_{27}N_5O_3$ | 62.32 | 7.06 | 18.17 | 61.91 | 6.98 | 17.96 |
| 15 | OH | $CO_2Et$ | 6 | 188–90 | $C_{14}H_{13}N_3O_4$ | 58.53 | 4.68 | 14.63 | 58.53 | 4.64 | 14.32 |
| 16 | $OC_2H_5$ | $COCH(CH_3)_2$ | 2A | 141–2 | $C_{17}H_{19}N_3O_3 \cdot H_2O$ | 61.62 | 6.39 | 12.68 | 61.47 | 6.30 | 12.78 |
| 17 | $OC_2H_5$ | CO-⟨cyclopropyl⟩ | 2A | 169–70 | $C_{17}H_{17}N_3O_3$ | 65.58 | 5.50 | 13.50 | 65.35 | 5.52 | 13.53 |
| 18 | $OC_2H_5$ | CO Ph | 2A | 212–4 | $C_{20}H_{17}N_3O_3$ | 69.15 | 4.93 | 12.10 | 68.81 | 4.99 | 12.15 |
| 19 | $OC_2H_5$ | $COCH_2CH_3$ | 2A | 155–6 | $C_{16}H_{17}N_3O_3$ | 64.20 | 5.72 | 14.06 | 64.05 | 5.72 | 14.00 |
| 20 | $OC_2H_5$ | CO-⟨cyclopentyl⟩ | 2A | 135–6 | $C_{19}H_{21}N_3O_3$ | 67.24 | 6.24 | 12.38 | 66.97 | 6.27 | 12.33 |
| 21 | $OC_2H_5$ | $CH_3$ | 22 | 251–3 | $C_{14}H_{15}N_3O_2$ | 65.36 | 5.88 | 16.33 | 65.19 | 5.90 | 16.32 |

TABLE 1-continued

| Example | R₁ | R₂ | Prepared as in Example | M.pt (°C.) | Formula | Calc. %C | Calc. %H | Calc. %N | Found %C | Found %H | Found %N |
|---|---|---|---|---|---|---|---|---|---|---|---|
| 22 | OC₂H₅ | Et | 22 | 145(d) | C₁₅H₁₇N₃O₂.HCl | 58.54 | 5.89 | 13.65 | 58.48 | 5.86 | 13.65 |
| 23 | OC₂H₅ | CONHCH₂CH₂N⟨⟩NCH₃ | 5B | 188-90 | C₂₁H₂₈N₆O₃.3HCl.2H₂O | 45.16 | 6.32 | 15.05 | 45.38 | 6.36 | 15.25 |
| 24 | OC₂H₅ | CONHCH₂CH₂N⟨⟩NCOOEt | 5B | 195(d) | C₂₃H₃₀N₆O₅.HCl | 54.49 | 6.16 | 16.58 | 54.37 | 6.18 | 16.49 |
| 25 | OC₂H₅ | CONHCH₂CH₂S—C(=NH)⊕Cl⊖NH₃ | 5B | 204-6 | C₁₇H₂₁ClN₆O₃S.H₂O | 46.10 | 5.23 | 18.97 | 46.09 | 4.89 | 18.94 |
| 26 | OC₂H₅ | COCMe₃ | 2A | 154-6 | C₁₈H₂₁N₃O₃ | 66.04 | 6.49 | 12.84 | 65.98 | 6.43 | 12.75 |
| 27A | OC₂H₅ | CO₂CH₂CH₂Br | 2A | 102-4° | C₁₆H₁₆BrN₃O₄ | 48.75 | 4.09 | 10.66 | 48.95 | 4.07 | 10.76 |
| 27B | OC₂H₅ | CO₂CH₂CH₂N⟨⟩O | 2B | 160°(d) | C₂₀H₂₄N₄O₅.2HCl | 50.85 | 5.33 | 11.86 | 50.45 | 5.48 | 11.76 |
| 28 | OC₂H₅ | COCH=CH₂ | 2A | 153-5° | C₁₆H₁₅N₃O₃ | 64.64 | 5.09 | 14.13 | 64.48 | 5.15 | 14.13 |
| 29 | OC₂H₅ | CO—cyclobutyl | 2A | 177-8° | C₁₈H₁₉N₃O₃ | 66.45 | 5.89 | 12.91 | 66.57 | 5.90 | 12.96 |
| *30 | OC₂H₅ | CONH(CH₂)₂NBu₂ | 5B | 126-30° | C₂₄H₃₅N₅O₃.½H₂O | 58.65 | 7.69 | 14.25 | 58.53 | 7.69 | 13.92 |
| 31 | OC₂H₅ | CO—nC₃H₇ | 2A | 165-6° | C₁₇H₁₉N₃O₃ | 65.16 | 6.11 | 13.41 | 65.08 | 6.07 | 13.39 |
| 32 | OC₂H₅ | COCF₃ | 2A | 209-210° | C₁₅H₁₂F₃N₃O₃.H₂O | 50.71 | 3.97 | 11.83 | 50.46 | 3.61 | 11.73 |
| 33 | O—CH₂—O—CO—cyclohexyl | CO₂Et | 2A | 133-4° | C₂₂H₂₅N₃O₆ | 61.82 | 5.90 | 9.83 | 61.85 | 5.91 | 9.80 |
| 34 | OC₂H₅ | COCHCl₂ | 2A | 220° | C₁₅H₁₃Cl₂N₃O₃ | 50.87 | 3.70 | 11.86 | 50.59 | 3.72 | 11.80 |
| 35 | OC₂H₅ | CH=CHCO₂Et | | 204-5° | C₁₈H₁₉N₃O₄ | 63.33 | 5.61 | 12.31 | 63.17 | 5.62 | 12.35 |
| 36 | OC₂H₅ | COCH₂Br | 2A | 189-93 | C₁₆H₁₆BrN₃O₃ | 50.81 | 4.26 | 11.11 | 50.84 | 4.23 | 11.21 |
| 37 | OC₂H₅ | CO Adamantyl | 2A | 224-5 | C₂₄H₂₇N₃O₃ | 71.09 | 6.71 | 10.36 | 71.09 | 6.66 | 10.26 |
| 38 | OC₂H₅ | COCH(CH₂)₃CH₃ / Et | 2A | 101-5 | C₂₁H₂₇N₃O₃.HCl | 62.14 | 6.95 | 10.35 | 61.96 | 6.91 | 10.40 |
| *39 | OC₂H₅ | CO₂CH₂CH₂N⟨⟩NMe 2HCl | 2B | 144 | C₂₁H₂₉Cl₂N₅O₄.3H₂O | 46.67 | 6.52 | 12.95 | 46.45 | 6.43 | 13.20 |

TABLE 1-continued

| Example | R₁ | R₂ | Prepared as in Example | M.pt (°C.) | Formula | Calc. %C | %H | %N | Found %C | %H | %N |
|---|---|---|---|---|---|---|---|---|---|---|---|
| *40 | OC₂H₅ | CO₂CH₂CH₂N⟨⟩·HCl | 2B | 210–2 | C₂₁H₂₆N₄O₄·2HCl·½H₂O | 52.02 | 6.13 | 11.55 | 51.91 | 5.78 | 11.40 |
| 41 | OC₂H₅ | COCO₂Et | 2A | 162–3 | C₁₇H₁₇N₃O₅ | 59.47 | 4.99 | 12.24 | 59.24 | 4.91 | 12.19 |
| 42 | OC₂H₅ | CONH₂ | 2A | 215–7 | | | | | | | |
| 43 | Oil | CO₂C₂H₅ (NH₃—C(CH₂OH)₃) | | 187–9 | C₁₄H₁₃N₃O₄·[NH₂—C(CH₂OH)₃] | 52.94 | 5.92 | 13.72 | 53.06 | 5.70 | 13.75 |
| 44 | OC₂H₅ | CHO | 44 | 200–2 | C₁₄H₁₃N₃O₃ | 61.99 | 4.83 | 15.49 | 61.67 | 4.85 | 15.57 |

EXAMPLE 22

Ethyl 5-ethyl-4,5-dihydroimidazo[1,2-a]quinoxaline-2-carboxylate hydrochloride

A suspension of 2.0 g of ethyl-4,5-dihydroimidazo[1,2-a]quinazoline-2-carboxylate in 100 ml of ethanol was treated with 10 ml of acetaldehyde and 1.0 ml of concentrated hydrochloric acid. The mixture was stirred at room temperature for 30 minutes and then hydrogenated over 0.2 g of 10% palladized carbon at atmospheric pressure for 2 days. The mixture was then filtered through "celite" and diluted with diethyl ether to give 1.5 g (60% yield) of ethyl 5-ethyl-4,5-dihydroimidazo[1,2-a]quinoxaline-2-carboxylate hydrochloride as colorless crystals after crystallization from methanol/ether.

The above method was also used for the preparation of the compound of Example 21.

EXAMPLE 44

Ethyl 5-formyl-4,5-dihydroimidazo[1,2-a]quinoxaline-2-carboxylate

A solution of 0.70 g of 98% formic acid in 70 ml of dichloromethane was stirred under dry nitrogen with 2.5 g of carbonyldiimidazole for 15 minutes and 1.4 g of ethyl 4,5-dihydroimidazo[1,2-a]quinoxaline-2-carboxylate were added. The mixture was stirred at room temperature for 6 hours under nitrogen and was then poured into ice/aqueous bicarbonate and filtered. The organic layer was dried over magnesium sulfate and evaporated under reduced pressure to a low volume. Dilution with ether gave 1.1 g (70% yield) of ethyl 4-formyl-4,5-dihydroimidazo[1,2-a]quinoxaline-2-carboxylate as colorless crystals after crystallization from dichloromethane/diethyl ether.

EXAMPLE 45

Tables were prepared containing 15 mg of the compound of Example 3 and sufficient excipient for one tablet weight of 100 mg. The excipient was lactose, starch, talc and magnesium stearate.

EXAMPLE 46

A dosed aerosol was prepared delivering per dose 2 mg of the compound of Example 3, 0.15 mg of emulsifier and 50 mg of propellant.

PHARMACOLOGICAL ACTIVITY

Passive cutaneous anaphylaxis of the rat (PCR)

Passive cutaneous anaphylaxis in the rat was carried out with male Wistar rats weighing 180–200 g which were sensitized by intradermal injection into four sites on the shaved back to produce a passive cutaneous reaction mediated by Ig G antibodies (a 4 hour sensitization following injection of antiserum heated at 56° C. for one hour). Antigen challenge was carried out in the same way; 1 mg of ovalbumen together with 0.5 ml of 1% Evans blue dye solution were injected intravenously and 30 minutes later, the animals were killed and the severity and area of each blue spot was scored when viewed from the reverse side of the skin. The inhibition observed following oral administration of the test compounds is given in Table II below:

TABLE II

| Compound of Example | % inhibition of Ig G PCR | |
|---|---|---|
| | 0.1 mg/kg | 1 mg/Kg |
| 3 | 26.3 | 67.5 |
| 4 | | 5.2 |
| 5B | | 33.8 |
| 6 | 19.0 | 61.1 |
| 7 | 32.5 | 49.4 |
| 8 | | 14.3 |
| 9 | 18.8 | 75.6 |
| 11 | | 44.0 |
| 12 | | 26.2 |
| 14 | 16.8 | 42.8 |

Various modifications of the compounds and compositions of the invention may be made without departing from the spirit or scope thereof and it should be understood that the invention is not intended to be limited to the specific embodiments.

What we claim is:

1. A compound selected from the group consisting of imidazoquinoxalines of the formula

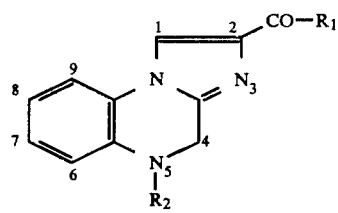 I wherein $R_1$ is selected from the group consisting of hydroxy, alkoxy of 1 to 5 carbon atoms and cyclohexylcarbonyloxymethoxy, $R_2$ is selected from the group consisting of alkoxycarbonylvinyl of 4 to 7 carbon atoms, —COR, —CONH(CH$_2$)$_n$—X and —A—(CH$_2$)$_m$—Y, R is selected from the group consisting of hydrogen, alkyl of 1 to 8 carbon atoms, cycloalkyl of 3 to 10 carbon atoms, alkenyl of 2 to 4 carbon atoms, alkoxy of 1 to 5 carbon atoms, alkoxycarbonyl of 2 to 5 carbon atoms, amino, —CF$_3$, —CHCl$_2$, phenyl, aralkyl of 7 to 10 carbon atoms, aralkoxy of 7 to 10 carbon atoms, n is 0 and X is phenyl or n is an integer from 1 to 5 and X is selected from the group consisting of

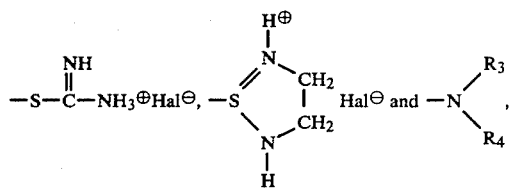

$R_3$ and $R_4$ are individually selected from the group consisting of hydrogen, alkyl of 1 to 5 carbon atoms, cycloalkyl of 3 to 7 carbon atoms, aryl of 6 carbon atoms and aralkyl of 7 to 8 carbon atoms or $R_3$ and $R_4$ taken together with the nitrogen atom to which they are attached form a saturated heterocycle with 4 to 8 ring carbon atoms optionally containing at least one nitrogen atom optionally substituted with alkyl of 1 to 3 carbon atoms or alkoxycarbonyl of 2 to 5 carbon atoms, Hal is chlorine, or bromine, A is selected from the group consisting of

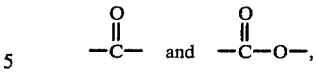

m is an integer from 1 to 3, Y is

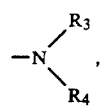

their non-toxic, pharmaceutically acceptable acid addition salts when $R_1$ is other than —OH and their salts with pharmaceutically acceptable metals or nitrogen bases when $R_1$ is OH.

2. A compound of claim 1 wherein $R_1$ is selected from the group consisting of —OH and alkoxy of 1 to 5 carbon atoms.

3. A compound of claim 2 wherein $R_2$ is selected from the group consisting of hydrogen, alkyl of 1 to 8 carbon atoms, —COR, —CONH—(CH$_2$)$_n$—X or —A—(CH$_2$)$_m$—Y and R is alkyl of 1 to 8 carbon atoms, cycloalkyl of 3 to 10 carbon atoms, vinyl, alkoxy of 1 to 5 carbon atoms, phenyl or benzyloxy, n is 2 and X is

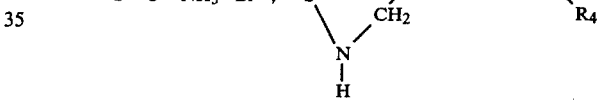

$R_3$ and $R_4$ are individually hydrogen, alkyl of 1 to 5 carbon atoms or $R_3$ and $R_4$ with the nitrogen atom form pyrrolidino, piperidino, piperazinyl, methylpiperazinyl or ethoxycarbonylpiperazinyl, A is —CO— or —CO$_2$—, m is 1 or 2.

4. A compound of claim 2 wherein $R_2$ is —COR and R is alkyl of 1 to 8 carbon atoms or alkoxy of 1 to 5 carbon atoms.

5. A compound of claim 1 which is diethyl 4,5-dihydroimidazo[1,2-a]quinoxalin-2,5-dicarboxylate.

6. A compound of claim 1 selected from the group consisting of 4,5-dihydro-5-ethoxycarbonylimidazo[1,2-a]quinoxaline-2-carboxylic acid and the tromethamine salt thereof.

7. A compound selected from the group consisting of

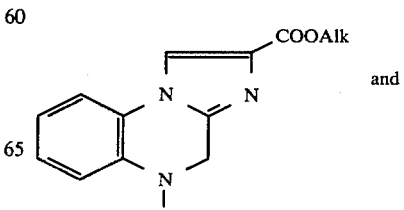

and

-continued

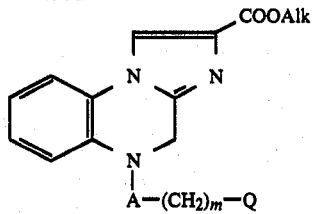

wherein Alk is alkyl of 1 to 5 carbon atoms, n' is 1 to 5, m is 1 to 3, A is —CO— or —COO— and Q is halogen.

8. An antiallergic composition comprising an antiallergically effective amount of at least one compound of the formula

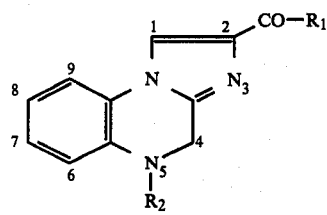

wherein $R_1$ is selected from the group consisting of hydroxy, alkoxy of 1 to 5 carbon atoms and cyclohexylcarbonyloxymethoxy, $R_2$ is selected from the group consisting of hydrogen, alkyl of 1 to 8 carbon atoms, alkoxycarbonylvinyl of 4 to 7 carbon atoms, —COR, —CONH(CH$_2$)$_n$—X and —A—(CH$_2$)$_m$—Y, R is selected from the group consisting of hydrogen, alkyl of 1 to 8 carbon atoms, cycloalkyl of 3 to 10 carbon atoms, alkenyl of 2 to 4 carbon atoms, alkoxy of 1 to 5 carbon atoms, alkoxycarbonyl of 2 to 5 carbon atoms, amino, —CF$_3$, —CHCl$_2$—, phenyl, aralkyl of 7 to 10 carbon atoms, aralkoxy of 7 to 10 carbon atoms, n is 0 and X is phenyl or n is an integer from 1 to 5 and X is selected from the group consisting of

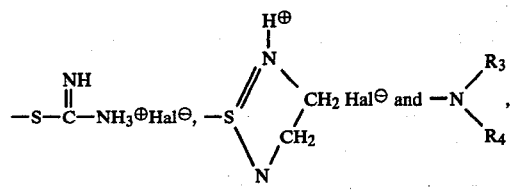

$R_3$ and $R_4$ are individually selected from the group consisting of hydrogen, alkyl of 1 to 5 carbon atoms, cycloalkyl of 3 to 7 carbon atoms, aryl of 6 carbon atoms and aralkyl of 7 to 8 carbon atoms or $R_3$ and $R_4$ taken together with the nitrogen atom to which they are attached form a saturated heterocycle with 4 to 8 ring carbon atoms optionally containing at least one sulfur atom or oxygen atom or nitrogen atom optionally substituted with alkyl of 1 to 3 carbon atoms or alkoxycarbonyl of 2 to 5 carbon atoms, Hal is chlorine or bromine A is selected from the group consisting of

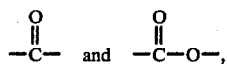

m is a integer from 1 to 3, Y is

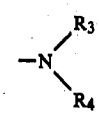

their non-toxic, pharmaceutically acceptable acid addition salts when $R_1$ is other than —OH and their salts with pharmaceutically acceptable metals or nitrogen bases when $R_1$ is —OH and a pharmaceutical carrier.

9. A composition of claim 8 wherein $R_1$ is selected from the group consisting of —OH and alkoxy of 1 to 5 carbon atoms.

10. A composition of claim 8 wherein $R_2$ is selected from the group consisting of hydrogen, alkyl of 1 to 8 carbon atoms, —COR, —CONH—(CH$_2$)$_n$—X or —A—(CH$_2$)$_m$—Y and R is alkyl of 1 to 8 carbon atoms, cycloalkyl of 3 to 10 carbon atoms, vinyl, alkoxy of 1 to 5 carbon atoms, phenyl or benzyloxy, n is 2 and X is

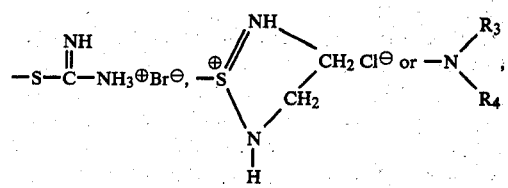

$R_3$ and $R_4$ are individually hydrogen, alkyl of 1 to 5 carbon atoms or $R_3$ and $R_4$ with the nitrogen atom form pyrrolidino, piperidino, piperazinyl, methylpiperazinyl or ethoxycarbonylpiperazinyl, A is —CO— or —CO$_2$—, m is 1 or 2.

11. A composition of claim 8 wherein $R_2$ is —COR and R is alkyl of 1 to 8 carbon atoms or alkoxy of 1 to 5 carbon atoms.

12. A composition of claim 8 wherein $R_2$ is —COR and R is alkyl of 1 to 8 carbon atoms or alkoxy of 1 to 5 carbon atoms.

13. A composition of claim 8 wherein the active compound is selected from the group consisting of 4,5-dihydro-5-ethoxycarbonylimidazo[1,2-a]quinoxaline-2-carboxylic acid and the tromethamine salt thereof.

14. A composition of claim 8 wherein the active compound is diethyl 4,5-dihydroimidazo[1,2-a]quinoxalin-2,5-dicarboxylate.

15. A method of preventing or relieving allergic symptoms in warm-blooded animals comprising administering to warm-blooded animals an antiallergically effective amount of at least one compound of the formula

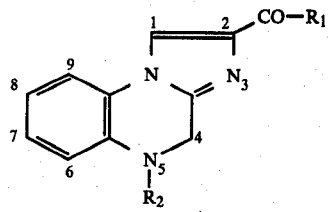

wherein $R_1$ is selected from the group consisting of hydroxy, alkoxy of 1 to 5 carbon atoms and cyclohexylcarbonyloxymethoxy, $R_2$ is selected from the group consisting of hydrogen, alkyl of 1 to 8 carbon atoms, alkoxycarbonylvinyl of 4 to 7 carbon atoms, —COR, —CONH(CH$_2$)$_n$—X and —A—(CH$_2$)$_m$—Y, R is selected from the group consisting of hydrogen, alkyl of 1 to 8 carbon atoms, cycloalkyl of 3 to 10 carbon atoms, alkenyl of 2 to 4 carbon atoms, alkoxy of 1 to 5 carbon atoms, alkoxycarbonyl of 2 to 5 carbon atoms, amino, —CF$_3$, —CHCl$_2$—, phenyl, aralkyl of 7 to 10 carbon atoms, aralkoxy of 7 to 10 carbon atoms, n is 0 and X is phenyl or n is an integer from 1 to 5 and X is selected from the group consisting of

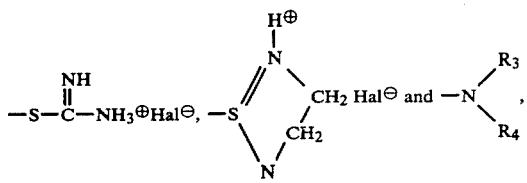

R$_3$ and R$_4$ are individually selected from the group consisting of hydrogen, alkyl of 1 to 5 carbon atoms, cycloalkyl of 3 to 7 carbon atoms, aryl of 6 carbon atoms and aralkyl of 7 to 8 carbon atoms or R$_3$ and R$_4$ taken together with the nitrogen atom to which they are attached form a saturated heterocycle with 4 to 8 ring carbon atoms optionally containing at least one sulfur atom or oxygen atom or nitrogen atom optionally substituted with alkyl of 1 to 3 carbon atoms or alkoxycarbonyl of 2 to 5 carbon atoms, Hal is chlorine or bromine A is selected from the group consisting of

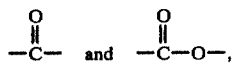

m is an integer from 1 to 3, Y is

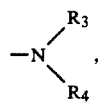

their non-toxic, pharmaceutically acceptable acid addition salts when R$_1$ is other than —OH.

16. A method of claim 15 wherein R$_1$ is selected from the group consisting of —OH and alkoxy of 1 to 5 carbon atoms.

17. A method of claim 15 wherein R$_2$ is selected from the group consisting of hydrogen, alkyl of 1 to 8 carbon atoms, —COR, —CONH—(CH$_2$)$_n$—X or —A—(CH$_2$)$_m$—Y and R is alkyl of 1 to 8 carbon atoms, cycloalkyl of 3 to 10 carbon atoms, vinyl, alkoxy of 1 to 5 carbon atoms, phenyl or benzyloxy, n is 2 and X is

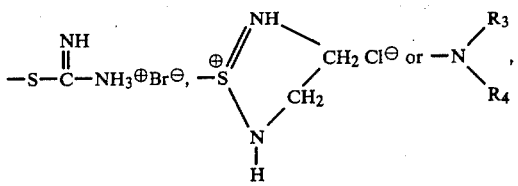

R$_3$ and R$_4$ are individually hydrogen, alkyl of 1 to 5 carbon atoms or R$_3$ and R$_4$ with the nitrogen atom form pyrrolidino, piperidino, piperazinyl, methylpiperazinyl or ethoxycarbonylpiperazinyl, A is —CO— or —CO$_2$—, m is 1 or 2.

18. A method of claim 15 wherein R$_2$ is —COR and R is alkyl of 1 to 8 carbon atoms or alkoxy of 1 to 5 carbon atoms.

19. A method of claim 14 wherein the active compound is diethyl 4,5-dihydroimidazo[1,2-a]quinoxaline-2,5-dicarboxylate.

20. A method of claim 14 wherein the active compound is selected from the group consisting of 4,5-dihydro-5-ethoxycarbonylimidazo[1,2-a]quinoxaline-2-carboxylic acid and the tromethamine salt thereof.

* * * * *

UNITED STATES PATENT AND TRADEMARK OFFICE
CERTIFICATE OF CORRECTION

PATENT NO. : 4,464,373          Page 1 of 3
DATED       : Aug. 7, 1984
INVENTOR(S) : ALAN C. BARNES It is certified that error appears in the above-identified patent and that said Letters Patent is hereby corrected as shown below:

Title page:

| Col. | Line | Title |
|---|---|---|
| [54] | | "[1,2,A]" should be --[1,2,a]-- |
| 3 | 5 | "$-S\overset{\overset{\oplus}{\phantom{.}}}{=}\genfrac{}{}{0pt}{}{NH}{\phantom{x}}\genfrac{}{}{0pt}{}{\phantom{x}}{CH_2}$ ... " should be -- (corrected structure) -- |
| 7 | 60 | " " " " " " " " " " " " |

UNITED STATES PATENT AND TRADEMARK OFFICE
CERTIFICATE OF CORRECTION

Page 2 of 3

PATENT NO. : 4,464,373
DATED : Aug. 7, 1984
INVENTOR(S) : ALAN C. BARNES et al

It is certified that error appears in the above-identified patent and that said Letters Patent is hereby corrected as shown below:

Co.

| 17 | Table 1 | 2nd Col. | "oil" should be --OH-- |
| --- | --- | --- | --- |
| 19 | Claim 1 | | should be |

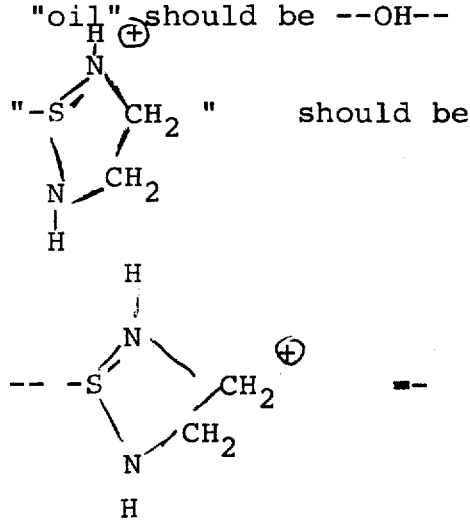

UNITED STATES PATENT AND TRADEMARK OFFICE
CERTIFICATE OF CORRECTION

PATENT NO. : 4,464,373                     Page 3 of 3
DATED      : Aug. 7, 1984
INVENTOR(S): ALAN C. BARNES et al It is certified that error appears in the above-identified patent and that said Letters Patent is hereby corrected as shown below:

| Col. | Line |
|------|------|
| 20   | Claim 3 |
| 22   | Claim 10 |
| 24   | Claim 17 |

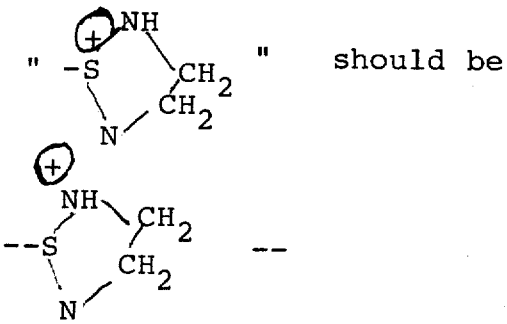

" " " " " " " " " " "

Signed and Sealed this

Second Day of April 1985

[SEAL]

Attest:

DONALD J. QUIGG

Attesting Officer      Acting Commissioner of Patents and Trademarks